(12) United States Patent
Horiba et al.

(10) Patent No.: US 8,288,343 B2
(45) Date of Patent: Oct. 16, 2012

(54) ACTIVATION OF ENDOTHELIAL NITRIC OXIDE SYNTHASE BY MIDKINE AND USES THEREFOR IN EFFECTING VASODILATION

(75) Inventors: Mitsuru Horiba, Nagoya (JP); Kenji Kadomatsu, Nagoya (JP); Itsuo Kodama, Nagoya (JP); Takashi Muramatsu, Aichi (JP); Hisaaki Ishiguro, Aichi (JP); Hiroharu Takenaka, Aichi (JP); Arihiro Sumida, Aichi (JP)

(73) Assignee: National University Corporation Nagoya University, Nagoya-Shi, Aichi (JP)

( * ) Notice: Subject to any disclaimer, the term of this patent is extended or adjusted under 35 U.S.C. 154(b) by 0 days.

(21) Appl. No.: 12/593,277

(22) PCT Filed: Mar. 28, 2008

(86) PCT No.: PCT/JP2008/000815
§ 371 (c)(1),
(2), (4) Date: Mar. 18, 2010

(87) PCT Pub. No.: WO2008/129851
PCT Pub. Date: Oct. 30, 2008

(65) Prior Publication Data
US 2010/0197577 A1    Aug. 5, 2010

(30) Foreign Application Priority Data

Mar. 30, 2007 (JP) ................................. 2007-093798

(51) Int. Cl.
*A61K 38/00* (2006.01)
*A61K 38/22* (2006.01)
*A61K 38/16* (2006.01)

(52) U.S. Cl. .................. 514/16.4; 514/5.3; 514/21.2

(58) Field of Classification Search .................. None
See application file for complete search history.

(56) References Cited

U.S. PATENT DOCUMENTS

2003/0185794 A1*  10/2003  Colley ................. 424/85.1
2005/0079151 A1*  4/2005   Ikematsu et al. ...... 424/85.1

FOREIGN PATENT DOCUMENTS

| EP | 1097717 A1 * | 5/2001 |
|---|---|---|
| JP | 08-027021 | 1/1996 |
| JP | 2005-068122 | 3/2005 |
| JP | 2006-188483 | 7/2006 |
| WO | WO-99/16463 | 4/1999 |
| WO | WO-99/53943 | 10/1999 |
| WO | WO-00/02578 | 1/2000 |
| WO | WO-2006/062087 | 6/2006 |
| WO | WO-2007/055397 | 5/2007 |

OTHER PUBLICATIONS

Villanueva et al. 2010. Free Radical Biol. and Med. 49:307-310.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Landry et al. 2001. NEJM 345:588-595.*
MGI-Mouse Facts, http://www.informatics.jax.org/mgihome/other/mouse_facts1.shtml, downloaded Mar. 10, 2011.*
Fearon et al., Catheterizations and Cardiovascular Interventions (2004) 61:422-428.
Gibson, American Heart Journal (2004) 148(5):S29-S33.
Henry et al., Circulation (2003) 107:1359-1365.
Horiba et al., Circulation (2006) 114:1713-1720.
International Search Report for PCT/JP2008/000815, mailed on Jul. 22, 2008, 4 pages.
International Preliminary Report on Patentability for PCT/JP2008/000815, issued on Oct. 13, 2009, 10 pages.
Kadomatsu et al., Biochemical and Biophysical Research Communications (1988) 151(3):1312-1318.
Keeley et al., New England Journal of Medicine (2007) 356:47-54.
Laham et al., Catheterizations and Cardiovascular Interventions (2003) 58:375-381.
Lopez et al., Cardiovascular Research (1998) 40:272-281.
Rogers et al., Journal of the American College of Cardiology (2000) 36(7):2056-63.
Simons et al., Circulation (2002) 788-793.
Tomomura et al., Journal of Biological Chemistry (1990) 265(18):10765-10770.
Tran et al., Biochemical and Biophysical Research Communications (2000) 276:830-836.

* cited by examiner

*Primary Examiner* — Shulamith H Shafer
(74) *Attorney, Agent, or Firm* — Morrison & Foerster LLP

(57) ABSTRACT

The object is to find a nitric oxide synthase activator, a method for the administration of the activator, and the amount of the activator to be administered. Disclosed is a nitric oxide synthase activator comprising a midkine family protein or a midkine derivative as an active ingredient. Specifically disclosed is a nitric oxide synthase activator which is intended to be administered through the blood, a coronary artery or a vein and which comprises a midkine family protein or a midkine derivative as an active ingredient.

7 Claims, 11 Drawing Sheets

CONTROL GROUP · MK ADMINISTRATION GROUP

CONTROL GROUP · MK ADMINISTRATION GROUP

PHODAMINE-MIDKINE (ISCHEMIC REGION)

PHODAMINE-MIDKINE (NON-ISCHEMIC REGION)

PHODAMINE-MIDKINE (MOUSE HEART)

PHODAMINE-MIDKINE
(TISSUES OTHER THAN MOUSE HEART)

LIVER                                          KIDNEY

ACTIVATION OF ENDOTHELIAL NITRIC OXIDE SYNTHASE BY MIDKINE AND USES THEREFOR IN EFFECTING VASODILATION

CROSS-REFERENCE TO RELATED APPLICATIONS

This application is the national phase of PCT application PCT/JP2008/000815 having an international filing date of 28 Mar. 2008, which claims benefit of Japanese application No. 2007-093798 filed 30 Mar. 2007. The contents of the above patent applications are incorporated by reference herein in their entirety.

TECHNICAL FIELD

The present invention relates to a nitric oxide synthase activator comprising a midkine family protein or a midkine derivative as an active ingredient.

BACKGROUND ART

Ischemic disorders are disorders caused by significant stagnation of blood supply to organs and tissues due to arteriosclerosis, organ transplantation, cardiovascular abnormality, arrest of bleeding during surgery, etc. It is known that exposure of organs and tissues in ischemic conditions to reoxygenation by reflow of blood (reperfusion) causes inflammatory reactions which induce ischemia-reperfusion injury. Particularly, myocardial tissue depends mainly on aerobic metabolisms, and its demanded oxygen is supplied from coronary arteries. The myocardial tissue, as compared with other tissues, requires higher oxygen consumption, and the oxygen uptake rate in the heart from coronary arterial blood, even at rest, is considered to be almost about 75% of the maximum. Accordingly, increase of myocardial oxygen demand in coronary circulation is hardly regulated by oxygen uptake rate and is regulated mainly by coronary blood flow.

As described above, cardiac muscle is vulnerable to ischemia, and that occlusion of coronary arteries by angiospasm, thrombus, arteriosclerosis etc. damages myocardial cells. As a result, the cardiac muscle undergoes an angina attack due to temporary ischemic conditions, and causes myocardial infarct due to long standing obstruction of blood flow. The heart disease resulting from myocardial ischemia is called an ischemic heart disease.

Therapy of ischemic heart disease has been carried out by drug treatments with therapeutic drugs which reduce cardiac load such as β-blockers and long-acting nitrate drugs and therapeutic drugs which have a coronary dilation activity such as calcium antagonists and nitrate drugs. Further, in therapy of e.g. acute myocardial infarct having a high mortality rate of around 30%, it is considered effective to administer thrombolytic agents, and to give reperfusion treatment such as percutaneous transluminal coronary angioplasty (PTCA or POBA), rotarblator, directional coronary atherectomy (DCA), coronary intervention with a stent and the like (see, for example, Non-Patent Documents 1, 2 and 3). These therapies ameliorate ischemic conditions, however there has been a problem that temporary ischemic conditions cause cell dysfunctions etc., and the functions of the heart are not completely recovered even if the ischemic conditions have been ameliorated. The heart diseases still remain major causes of death in the world, and there has been demand for more effective therapeutic drugs.

It is known that although large coronary artery constriction is relieved by reperfusion therapy such as coronary intervention, subsequently occurred severe inflammatory reactions, apoptosis, etc., due to recanalization, damage cardiac muscle (reperfusion damage) or subsequently manifested lethal arrhythmia causes sudden death, and thus the death rate in hospitals is as high as about 10% even after treatment. Even in the case reperfusion therapy has been successful if extensive myocardial damage remains, severe heart malfunction may readily cause cardiac failure and patients are accompanied by the risk of sudden death from lethal arrhythmia. It is thus considered extremely important to prevent, by initial therapy at the acute stage, reperfusion injury and spread of an injured area. The cause of reperfusion injury has been considered to lie in activation of inflammatory cells such as neutrophils and in transient enhanced expression of cytokines and adhesion molecules by vascular endothelial cells, but a true target for preventing or treating the reperfusion injury has not been found.

Nitric oxide synthase (NOS) is an enzyme that uses L-arginine as a substrate to produce nitric oxide (NO), and known as neuronal NOS (n-NOS), inducible NOS (i-NOS), and endothelial NOS (eNOS). NO produced by eNOS is distributed mainly in vascular endothelial cells and activates soluble guanylate cyclase in vascular smooth muscle cells to promote increases in cGMP, thereby relaxing the blood vessels. It has been reported that, in ischemic disorders and ischemia-reperfusion injury, NO derived from eNOS has protective effects on blood vascular systems, such as a platelet aggregation inhibiting effect, an effect of inhibiting the adhesion and infiltration of leukocytes into vascular endothelium (inhibitory action on expression of adhesion molecules), an NF-κB activity-inhibiting effect, an inhibitory effect on growth of vascular smooth muscle cells, a superoxide scavenger effect, etc. It is known that, after reperfusion, vascular endothelial cells are damaged and the eNOS-mediated production of NO is reduced. Supply of a suitable amount of NO during an ischemia (reperfusion) period may permit maintenance of blood flow in a border zone between local ischemia and normal tissue and may suppress cell dysfunctions by regulating infiltration with inflammatory cells, and thus has drawn the interest as a therapeutic method for ischemia (reperfusion).

Midkine (referred to hereinafter as "MK") is a cell growth factor or a cell differentiation factor found as a gene product expressed transiently in a process of differentiation induction of embryonal cancer cells by retinoic acid, and is a basic amino acid- and cysteine-enriched polypeptide with a molecular weight of 13 kDa (see, for example, Non-Patent Documents 4 and 5). The amino acid sequence of MK has 50% homology with pleiotrophin (PTN), and these proteins are considered as heparin-binding family proteins. The inventors previously found that MK is effective in prevention and treatment of the above-mentioned ischemic cell dysfunction and/or myocardial cell dysfunction after ischemia-reperfusion (see Patent Document 1), and also that the preventive and therapeutic effect of MK on the ischemic cell dysfunction and/or myocardial cell dysfunction after ischemia-reperfusion is based partly on its apoptosis-suppressing action (see Patent Documents 2, 3 and 4 and Non-Patent Document 6). PTN that is a family protein of MK has been reported to have an angiogenic activity, and MK, similar to the family protein PTN, has been considered to have an angiogenic activity (see Patent Document 5).

The inventors have previously administered MK to a model mouse via an osmotic pump in verifying the therapeutic effect of MK on myocardial cell dysfunction after ischemia-reperfusion based on MK's apoptosis-suppressing action (see Patent Document 4). The administration via an osmotic pump is easily utilized in the in vivo evaluation of the effectiveness of the drug, but cannot be used in actual human treatment, and therefore, there has been necessity for establishment of the optimum method of administration to be applied to human treatment or prevention.

In the treatment of ischemic heart disease by a cell growth factor, it has been reported that because the drug, hardly reaches cardiac muscle by intravascular administration such as intracoronary administration and intravenous administration, and can thus not achieve a sufficient effect (see Non-Patent Documents 7 and 8). In order to increase the efficiency of incorporation of the drug into cardiac muscle, various administration ways such as direct injection into cardiac muscle, high-pressure retrograde administration to coronary veins (see Non-Patent Document 9) and rapid injection into coronary arteries (Non-Patent Documents 10 and 11) have been devised and verified. However, these administration ways are complicated and hardly practically usable, and their effect is not sufficient. Thus, an efficient administration method has not been found, and an easy and therapeutically effective administration method is needed.

Patent Document 1: International Publication No. 1999/16463
Patent Document 2: International Publication No. 2000/02578
Patent Document 3: JP-A 2005-68122
Patent Document 4: International Publication No. 2006/062087
Patent Document 5: International Publication No. 1999/053943
Non-Patent Document 1: The New England Journal of Medicine (2007); 356: 47-54
Non-Patent Document 2: J. Am. Coll Cardio. (2000); 36: 2056-63
Non-Patent Document 3: Am. Heart J. (2004); 148: S29-33
Non-Patent Document 4: Kadomatsu, K. et al.: (1988) Biochem. Biophys. Res. Commun., 151: p. 1312-1318
Non-Patent Document 5: Tomokura, M. et al.: (1999) J. Biol. Chem. 265: p. 10765-10770
Non-Patent Document 6: Mitsuru Horiba, et al.: (2006) Circulation, 114: p. 1713-1720
Non-Patent Document 7: M. Roger J. Laham, et al.: (2003) Catheterization and Cardiovascular Interventions, 58: p. 375-381
Non-Patent Document 8: Timothy D. Henry, et al.: (2003) Circulation, 107: p. 1359-1365)
Non-Patent Document 9: William F. Fearon, et al.: (2004) Catheterization and Cardiovascular Interventions, 61: p. 422-428
Non-Patent Document 10: Michael Simons, et al.: (2002) Circulation, 105: p. 788-793
Non-Patent Document 11: John J. Lopez, et al.: (1998) Cardiovascular Research, 40: p. 272-281

DISCLOSURE OF INVENTION

The object of the present invention is to find an eNOS activator, a method and an amount of administration thereof.

The inventors found that MK has an effect of activating eNOS by acting on vascular endothelial cells exposed to hypoxic conditions. Also, the inventors found that MK activates eNOS and the eNOS derive NO, which cause vasodilation. Further, the inventors found that blood pressure is reduced by administering MK. From these findings, the inventors completed the present invention that MK can be utilized in vasodilation and blood-flow maintenance in ischemia and ischemia-reperfusion and also can be utilized in prevention and/or treatment of injury in ischemia-reperfusion.

Further, the inventors detected that topical administration of MK dramatically ameliorate ischemic heart disease and ischemia-reperfusion injury. Particularly, the inventors discovered that MK administered intracoronarily to a model animal with ischemic myocardial cell dysfunction accumulates specifically in ischemic dysfunction region, and that MK has an ability to accumulate in the ischemic dysfunction site. Further examination, the inventors surprisingly found that the accumulation of MK in the ischemic dysfunction site is observed not only in local administration to the ischemic region but also in administration to the blood at a site apart from the ischemic region. More specifically, the inventors found that MK administered intravenously to a model animal induced ischemic cell dysfunction accumulates specifically in the ischemic dysfunction site. Particularly, the inventors observed that when MK was administered intravenously to a model animal induced ischemic myocardial cell dysfunction, MK specifically accumulated in the ischemic dysfunction site of the heart, while MK didn't accumulate in the non-dysfunction site of the heart and in other organs, which showed the excellent ability of MK to accumulate in the ischemic dysfunction site, and the present invention was thereby completed.

The present invention relates to a nitric oxide synthase activator comprising a midkine family protein or a midkine derivative as an active ingredient, as well as a therapeutic agent for ischemic disorders comprising a midkine family protein or a midkine derivative as an active ingredient, which is administered to the blood. More specifically, the present invention relates to the following inventions:

(1) A nitric oxide synthase activator comprising a midkine family protein or a midkine derivative as an active ingredient.

(2) The nitric oxide synthase activator according to (1), which is to treat or prevent a cell dysfunction due to ischemia or ischemia-reperfusion.

(3) The nitric oxide synthase activator according to (2), wherein the cell dysfunction due to ischemia or ischemia-reperfusion is a myocardial cell dysfunction due to ischemia or ischemia-reperfusion.

(4) The nitric oxide synthase activator according to any one of (1) to (3), wherein the midkine family protein or the midkine derivative is midkine or pleiotrophin.

(5) A vasodilator comprising a midkine family protein or a midkine derivative as an active ingredient.

(6) The vasodilator according to (5) for use in treatment or prevention of a cell dysfunction due to ischemia or ischemia-reperfusion.

(7) The vasodilator according to (5) or (6), which is a coronary dilator.

(8) The vasodilator according to any one of (5) to (7), wherein the midkine family protein or the midkine derivative is midkine or pleiotrophin.

(9) A blood pressure depressant comprising a midkine family protein or a midkine derivative as an active ingredient.

(10) The blood pressure depressant according to (8), which is to treat or prevent a cell dysfunction due to ischemia or ischemia-reperfusion.

(11) The vasodilator according to (9) or (10), wherein the midkine family protein or the midkine derivative is midkine or pleiotrophin.

(12) A therapeutic or prophylactic agent for an ischemic disorder or ischemia-reperfusion injury comprising a midkine family protein or a midkine derivative as an active ingredient, wherein the agent activates nitric oxide synthase.

(13) The therapeutic or prophylactic agent according to (12), wherein the ischemic disorder or the ischemia-reperfusion injury is an ischemic heart disease or myocardial ischemia-reperfusion injury.

(14) The therapeutic or prophylactic agent according to (12), wherein the ischemic disorder or the ischemia-reperfusion injury is cardiac failure, myocardial infarct or angina pectoris.

(15) The therapeutic or prophylactic agent according to any one of (12) to (14), which is administered to the blood.

(16) The therapeutic or prophylactic agent according to any one of (12) to (14), which is administered intravenously or intracoronarily.

(17) The therapeutic or prophylactic agent according to any one of (12) to (16), wherein the midkine family protein or the midkine derivative is midkine or pleiotrophin.

(18) A therapeutic or prophylactic agent for an ischemic disorder or a cell dysfunction after ischemia-reperfusion comprising a midkine family protein or a midkine derivative as an active ingredient, which is for administration to the blood.

(19) A therapeutic or prophylactic agent for an ischemic disorder or a cell dysfunction after ischemia-reperfusion comprising a midkine family protein or a midkine derivative as an active ingredient, which is for intravenous or intracoronary administration.

(20) The therapeutic or prophylactic agent according to (18) or (19), wherein the ischemic disorder or the cell dysfunction after ischemia-reperfusion is an ischemic heart disease or a myocardial cell dysfunction after ischemia-reperfusion.

(21) The therapeutic or prophylactic agent according to any one of (18) to (19), wherein the midkine family protein or the midkine derivative is midkine or pleiotrophin.

(22) The therapeutic or prophylactic agent according to any one of (1) to (21), which is administered in an amount of 50 ng/kg to 100 pg/kg.

In the present invention, "midkine family protein" refers to a protein or peptide which has a sequence similar to MK or a site of MK expressing functions and which has functions similar to MK. Because evolutionarily close proteins are not always highly homologous in amino acid sequence as a whole, proteins having functions similar to MK are included in the MK family protein even if they have low level of amino acid sequence homology to MK. Such proteins or peptides with different overall amino acids length from MK are also included in the MK family protein. The MK family protein includes, for example, MK, MK-like proteins (see International Publication No. 2004/052928), and PTN (50% homology to MK). The MK family protein includes proteins or peptides having high level of homology to MK as well as one or more functions of MK and proteins or peptides hybridizing with MK under stringency conditions as well as one or more functions of MK.

In the above description, the wording "high level of homology to MK" means structure similarity to MK. The structure as used herein refers to primary structure (amino acid sequence), secondary structure or tertiary structure. Preferably, proteins or peptides having high level of homology to MK in primary structure (amino acid sequence) as well as one or more functions of MK have 20% or more homology to MK, more preferably 30% or more homology, even more preferably 40% or more homology, still more preferably 50% or more, even still more preferably 60% or more, 70% or more, 80% or more, 90% or more, 95% or more, or 98% or more in amino acid sequence. The homology in amino acid sequence can be determined by using known programs such as BLAST, FASTA etc. The steric structure of MK has already been reported (Iwasaki, W. et al.: (1997) EMBO J. 16, p. 6936-6946), and the homology to MK in secondary or tertiary structure can be determined with homology modeling such as PSI-BLAST, HMMER, 3D-1D, and threading. The similarities of those proteins or peptides having high level of homology in secondary or tertiary structure as well as one or more functions of MK are preferably 40% or more, more preferably 50% or more, even more preferably 60% or more, 70% or more, 80% or more or 90% or more.

In the above description, the wording "hybridizing with MK" means to hybridize with MK under hybridization conditions used ordinarily by those skilled in the art. For example, a condition described in Molecular Cloning, A Laboratory Manual, Second Edition, Cold Spring Harbor Laboratory Press (1989) can be employed.

In the present invention, the term "midkine derivative" refers to an artificially produced or naturally occurring MK-derived substance which exhibits functions of MK as it is or after being degraded in the living body, which include MK variants or mutants with amino acid sequence of MK wherein amino acids are substituted, deleted, or added, and also include MK derivatives that is chemically modified MK as well as MK prodrugs. In the MK variants or mutants with amino acids sequence of MK wherein amino acids are substituted, deleted, or added the number of substituted, deleted or added amino acids is preferably 1 to 30, more preferably 1 to 20, even more preferably 1 to 10, still more preferably 1 to 5, and most preferably 1 to 3. Such MK derivatives can include, for example, sugar-modified MK (see, for example, JP-A 2000-184891), sugar-unmodified MK, variants or mutants of MK in which several amino acids have been substituted, deleted or added, chemically modified MK, truncated MK (see U.S. Serial. No. 2004/0219614), a C-fragment of MK (a C-terminal peptide consisting of amino acids positions 62 to 121 of MK), an N-fragment of MK (an N-terminal peptide consisting of amino acids positions 1 to 52 of MK), a C-domain of MK (a peptide consisting of amino acids positions 62 to 104 of MK), an N-domain of MK (a peptide consisting of amino acids positions 15 to 52 of MK), an N-tail of MK (a peptide consisting of amino acids positions 1 to 14 of MK), and a C-tail of MK (a peptide consisting of amino acids positions 105 to 121 of MK).

In the above description, the "functions of MK" are not particularly limited as long as MK exhibit. Examples of such functions include a cell growth function, an apoptosis suppressing function, a heparin binding ability, a cell migration ability, a differentiation inducing ability, and an eNOS activating function. The function of MK is preferably an apoptosis suppressing function or an eNOS activating function, more preferably an eNOS activating function.

In the present invention, the "nitric oxide synthase activator" is not particularly limited as long as it is used for the purpose of activating NOS. The "nitric oxide synthase activator" in the present invention is preferably an endothelial nitric oxide synthase (eNOS) activator. The nitric oxide synthase activator in the present invention includes any nitric oxide synthase activator used for the purpose of activating NOS whether explicitly stated or not. For example, the nitric oxide synthase activator of the present invention encompasses drugs that utilize the action of NO produced by the activated nitric oxide synthase. Such drugs can include, for example, a platelet aggregation inhibitor, an adhesion molecule expression inhibitor, an NF-κB activity inhibitor, a growth inhibitor of vascular smooth muscle cell, a superoxide scavenger, a vessel protecting agent, a vasodilator, an agent for cell dysfunction due to ischemia or ischemia-reperfusion, and an agent for ischemic disorder, preferably a vasodilator, an agent for cell dysfunction due to ischemia or ischemia-reperfusion, and an agent for ischemic heart disease.

In the present invention, the "cell dysfunction due to ischemia or ischemia-reperfusion" refer to dysfunctions of vascular endothelial cells or cells constituting organs that are caused by occlusion of blood flow due to arteriosclerosis, vasospasm, thrombus, organ transplantation, cardiovascular abnormality, arrest of bleeding during surgical operation, etc. Examples of such dysfunctions include cell membrane damage, mitochondria edema, cell edema, cell necrosis, apoptosis, etc. The cell dysfunction due to ischemia-reperfusion is known not only in an ischemic area but also in distant organs, and the cell dysfunction due to ischemia-reperfusion in the present invention is not limited to dysfunctions in ischemic organs.

In the present invention, the "cell dysfunction due to myocardial ischemia or ischemia-reperfusion" is cell dysfunction due to ischemia or ischemia-reperfusion caused by ischemic conditions or recovery from ischemic conditions of cardiac muscle, wherein coronary arteries are occluded or blocked by arteriosclerosis, vasospasm, thrombus, organ transplantation, cardiovascular abnormality, arrest of bleeding during surgical operation, etc. The "cell dysfunction due to myocardial ischemia or ischemia-reperfusion" in the present invention is not limited to cell dysfunction in cardiac muscle, and encompasses systemic cell dysfunction as long as the cell dysfunction is caused by myocardial ischemia or ischemia-reperfusion.

In the present invention, the "ischemic disorder" refers to a disorder causing ischemia, wherein blood vessels are occluded or blocked by vasospasm, thrombus, arteriosclerosis or the like. Organs in which ischemia is caused include, for example, the brain, heart, periphery, spinal cord, kidney, liver, and intestinal tract (colon). The ischemic disorder includes, for example, ischemic brain diseases such as cerebral infarct; apoplexy and ischemic heart diseases such as myocardial infarct; arteriosclerosis obliterans; postischemic acute renal failure; hepatic warm ischemia reperfusion damage; ischemic bowel disease; and ischemic colitis, and preferably is the ischemic heart diseases.

In the present invention, the "ischemic heart disease" refers to a disease wherein coronary ischemia occurs due to vasospasm, thrombus, arteriosclerosis or the like. Examples of the disease include angina pectoris (unstable angina, stable angina, vasospastic angina pectoris), myocardial infarct (ST-elevation myocardial infarct, non-ST-elevation myocardial infarct), asymptomatic myocardial ischemia, ischemic cardiomyopathy, and ischemic heart failure. Vascular restenosis generated after reperfusion by cancellation of ischemic conditions is also included in diseases of coronary ischemia, and is included in the ischemic heart disease of the present invention. The ischemic heart disease of the present invention includes irreversible myocardial damage during severe ischemia due to severe stenosis or occlusion of coronary arteries, as well as diseases caused by the irreversible myocardial damage.

In the present invention, the "myocardial ischemia-reperfusion injury" is an injury generated by resumption of blood flow in a heart after transient ischemic conditions. The cause for the ischemia includes, for example, aortic occlusion in cardiac surgery, angina pectoris, myocardial infarct, and transient myocardial ischemia due to storage of donor's heart at the time of heart transplantation. The injury includes, for example, cell membrane damage, mitochondria edema, cell edema, cell necrosis, apoptosis, cardiocyte death, loss of myocardial contractility, arrhythmia, no-reflow phenomenon, and heart failure.

The wording "administrated to the blood" in the present invention means that the therapeutic or prophylactic drug of the present invention is intended to be administrated to the blood. The method of administration to the blood is not particularly limited as long as it can be used for administration to the blood. For example, the drug can be administered by means of an injection, drip infusion via a winged needle or an indwelling needle, or a catheter. The site through which the drug is administered may be a vein or an artery, and the vein or artery includes a coronary artery, a peripheral vein such as an arm vein, and a central vein such as a superior caval vein or a postcaval vein.

The nitric oxide synthase activator of the present invention comprising a midkine family protein or a midkine derivative as an active ingredient activates NOS (particularly eNOS) and is thus useful in therapy or prophylaxis of diseases and symptoms (particularly ischemic disorder) ameliorated by production of NO. Particularly, the nitric oxide synthase activator of the present invention comprising a midkine family protein or a midkine derivative as an active ingredient accumulates in an ischemic disorder site after administration to the blood and is thus useful as a therapeutic or prophylactic drug with fewer side effects such as migraine caused by NO.

BEST MODE FOR CARRYING OUT THE INVENTION

Figure 1:
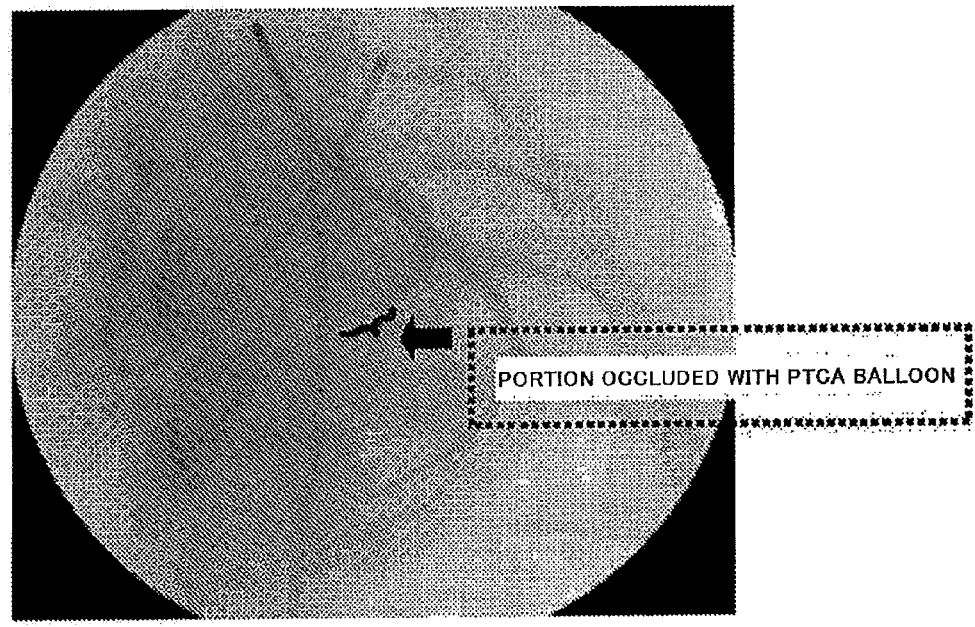
FIG. 1 is a photograph showing an occluded site of a coronary artery with a catheter balloon.

The MK family protein or the MK derivative in the present invention can be obtained by introducing an expression vector including a cDNA encoding the MK family protein of the MK derivative into *Escherichia coli*, yeasts, insect cells, animal cells or the like, and then expressing the cDNA. For example, when MK is used as a cell growth factor or an apoptotic suppressor, MK can be prepared as a recombinant MK by integrating an MK-encoding DNA into an expression vector and introducing the vector into *Pichia* yeast to express it, and collecting the recombinant MK (see JP-A 9-95454).

The drug of the present invention, when used as a medicine, maybe administered alone or in combination with another drug. The drug that can be used in combination with the drug of the present invention is not particularly limited as long as it is a drug that does not eliminate the effect of the therapeutic or prophylactic drug of the present invention. Preferably, examples of such drug include therapeutic or prophylactic drugs for heat diseases and therapeutic or prophylactic drugs inhibiting thrombus formation, for example, β-blockers, long-acting nitrate drugs, calcium antagonists, nitrate drugs, urokinase, streptokinase, and tissue plasminogen activator (t-PA).

The dosage form of the drug of the present invention is preferably an injection but not particularly limited as long as it can be administered to a patient. The dosage form of the drug of the present invention can include, for example, a liquid and a lyophilized formulation. When the drug of the present invention is used as an injection, the injection may contain additives as necessary, for example, solubilizing agents such as propylene glycol and ethylene diamine, buffer agents such as phosphates, tonicity agents such as sodium chloride and glycerin, stabilizers such as sulfites, preservatives such as phenol, and soothing agents such as lidocaine (see "Iyakuhin Tenkabutsu Jiten" (Medicinal Additive Dictionary) published by Yakuji Nippo Limited and Handbook of Pharmaceutical Excipients, Fifth Edition, published by APhA Publications). When the therapeutic or prophylactic drug of the present invention is used as an injection, a storage container used includes an ampoule, a vial, a pre-filled syringe, a cartridge for a pen-shaped syringe, and a bag for intravenous drip.

The method of administering the drug of the present invention is not particularly limited as long as the desired therapeutic or prophylactic effect can be obtained. Preferably, the drug is administered to the blood or cardiac muscle. Specifically, the drug can be administered intravascularly (for example, intravenously or intracoronarily) or to cardiac muscle of an ischemic region. The method of administering the drug of the present invention includes intravenous injection of an injection or intravenous drip infusion, intravenous or intraarterial administration via a catheter, and intramyocardial administration by an intramuscular injection via a catheter. The drug of the present invention can be administered before reperfusion, throughout reperfusion, or after reperfusion. When the drug of the present invention is used as a prophylactic drug, it is administered preferably either before reperfusion or throughout reperfusion. The drug of the present invention may be administered all at once, continuously or intermittently. For example, the drug of the present invention may be administered continuously for 1 minute to 2 weeks. The method of administering the drug of the present invention is preferably either continuous administration for 5 minutes to 1 hour throughout reperfusion or continuous administration for 5 minutes to 1 hour after reperfusion, more preferably either continuous administration for 5 to 15 minutes throughout reperfusion or continuous administration for 5 to 15 minutes after reperfusion.

The amount of the drug of the invention to be administered is not particularly limited as long as the desired therapeutic or prophylactic effect can be obtained, and the amount can be determined appropriately depending on the symptoms, sex, age etc. of the patient. The amount of the therapeutic or prophylactic agent of the invention to be administered can be determined for example on the basis of an indicator of its therapeutic or prophylactic effect on ischemic disorder or ischemia-reperfusion injury. The amount of the therapeutic or prophylactic agent of the invention to be administered is preferably 1 ng/kg to 10 mg/kg, more preferably 10 ng/kg to 1 mg/kg, even more preferably 50 ng/kg to 500 μg/kg, still more preferably 50 ng/kg to 100 μg/kg, further more preferably 50 ng/kg to 50 μg/kg, and most preferably 50 ng/kg to 5 μg/kg.

EXAMPLES

Example 1

Therapeutic Effect of Intracoronary Administration of MK on Myocardial Cell Dysfunction After Ischemia-Reperfusion (Administration Throughout Occlusion)

(1) Preparation of MK

Human MK mRNA was prepared from Wilms' tumor-derived cultured cell strain G-401 (Tsutui, J. et al., Biochem. Biophys. Res. Commun. 176, 792-797, 1991). 30 cycles of PCR were carried out to prepare a human MK cDNA having an EcoRI recognition site at both ends of an MK coding region. One cycle of the PCR consists of a temperature change of 93° C.→37° C.→72° C. A sense PCR primer (5'-GCGGAATTCATGCAGCACCGAGGCTTCCTC-3') and an antisense PCR primer (5'-GCGGAATTCCTAGTC-CTTTCCCTTCCCTTT-3') which were designed so as to contain a sequence (5'-GAATTC-3') recognized by a restriction enzyme EcoRI were used as primers. The human MK mRNA was used as a template.

The MK cDNA expression vector pHIL301 (histidine and neomycin resistance genes-containing expression vector; see JP-A 2-104292 and EP Patent Publication No. 0339568) for expression in an yeast *Pichia pastoris* GS115 (referred to hereinafter as "*Pichia* yeast GS115") were digested with a restriction enzyme EcoRI and then ligated to each other with a ligation kit (Takara Bio) to prepare a recombinant expression vector.

By the electroporation method, the recombinant expression vector prepared above was introduced into *Pichia* yeast GS115 (Invitrogen). The *Pichia* yeast GS115 into which the vector had been introduced was cultured in a histidine-free medium containing G418, thereby giving a plurality of clones having the objective MK gene. The resulting clones were cultured under induction with methanol. The culture supernatant was collected and analyzed by western blotting with rabbit anti-mouse MK polyclonal antibody to confirm whether or not the clones secreted MK.

One clone secreting MK into a culture supernatant was designated as T3L-50-4P, and this clone was cultured (see JP-A 7-39889). Its culture supernatant was recovered and then purified by ion-exchange chromatography and affinity chromatography on a heparin column, to give high-purity MK.

(2) Creation of an Ischemic Model Animal and Administration of MK

Anesthesia management of a pork pig (male, about 40 kg) was performed by inhalation of isoflurane after endotracheal intubation. After an M-mode image was recorded by cardiac ultrasonography (echocardiography), a pig tail catheter was indwelled in the left ventricle, and the left ventricular end diastolic pressure (LVEDp) was measured. Coronary angiography, left ventriculography (LVG), and measurement of the pressure in the left ventricle were performed, and then the left coronary artery between D1 and D2 was occluded for 45 minutes with a balloon catheter for PTCA (FIG. 1). 40 minutes after occlusion, administration of MK (50 ng/kg, 5 μg/kg) via the lumen of a PTCA wire into the coronary artery was initiated, and was continued for 10 minutes until 5 minutes passed after relief of occlusion. A control group was administered continuously with the same volume of physiological saline in the same manner. After administration was finished, echocardiography was performed. LVEDp was measured with the pig tail catheter. Further, coronary angiography, LVG, and measurement of the pressure in the left ventricle were performed. In addition, a blood test was carried out every 2 hours.

On the next day, anesthesia management of the animal was performed again by inhalation of isoflurane after endotracheal intubation. After an M-mode image was recorded by echocardiography, LVEDp was measured with the pig tail catheter. Further, coronary angiography, LVG, measurement of the pressure in the left ventricle, and blood test were performed. Thereafter, thoracotomy was performed, a photograph was taken, beating of the heart was stopped with potassium chloride, and the heart was excised. The occluded part of the coronary artery in the excised heart was ligated, and 5 mL of 5% Evans blue was injected in a retrograde fashion via the void part of an aortic arch, thereby staining the non-ischemic portion. Thereafter, the left ventricle was sliced into 5 sections, and the ischemic risk region of the left ventricle was stained with triphenyl tetrazolium chloride (TTC).

(3) Results

The results of 5 μg/kg administration are shown in FIGS. 2 to 13. In the following results, $p<0.05$ as compared with the control group was judged to be significant. Even by 50 ng/kg administration, an effect of preventing deterioration of symptoms can be obtained (not shown).

Figure 2:
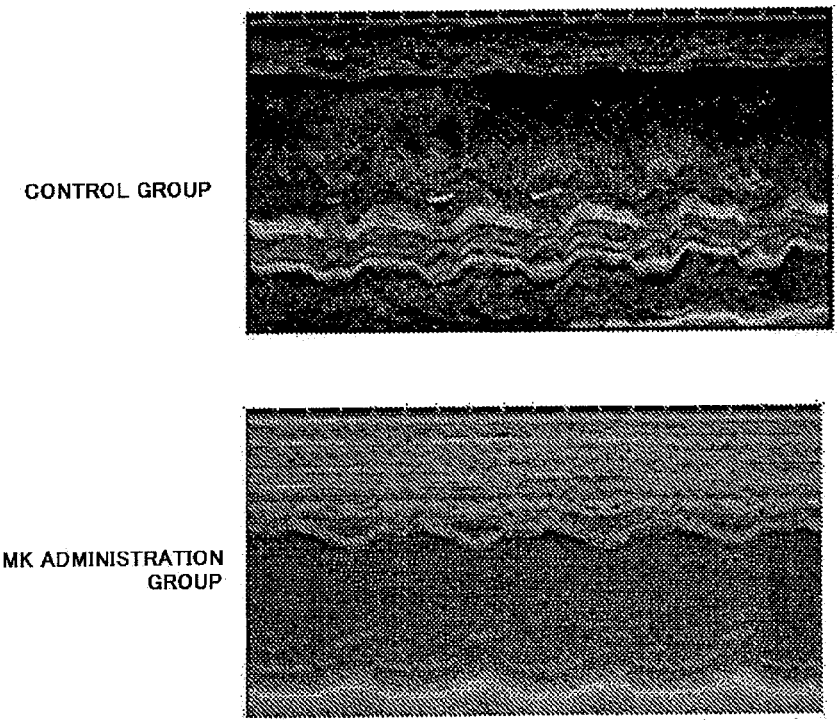
FIG. 2 is a photograph showing a result of cardiac ultrasonography.
Figure 3:
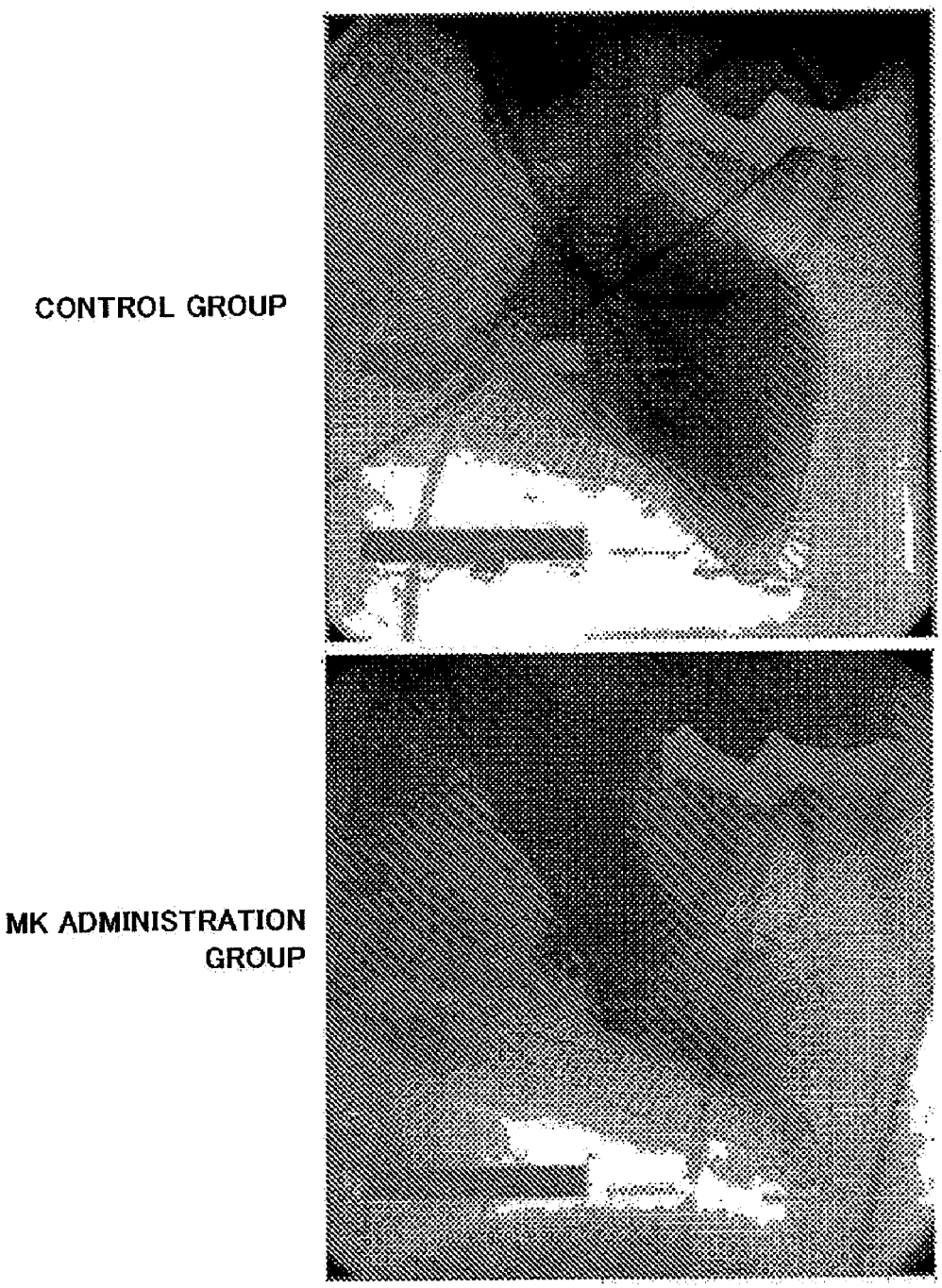
FIG. 3 is a photograph showing a result of left ventriculography. The portion shown by a red line shows the left ventricle in diastole, and the portion shown by a blue line shows the left ventricle in systole.

The result of cardiac ultrasonography is shown in FIG. 2. In the cardiac ultrasonography, cardiac functions of the MK treatment group were significantly ameliorated as compared with the non-treatment group. The result of left ventriculography is shown in FIG. 3. In the left ventriculography, the MK treatment group was excellent in heart wall motion as compared with the non-treatment group. Further, the MK treatment group showed a significant therapeutic effect in respect of the left ventricular end-diastolic pressure, the systolic maximum pressure increase rate, the cardiac output, etc. as compared with the non-treatment group. From these results, it was revealed that the loss of cardiac functions by myocardial cell dysfunction due to ischemia and reperfusion is suppressed by administration of MK to the blood.

Figure 4:
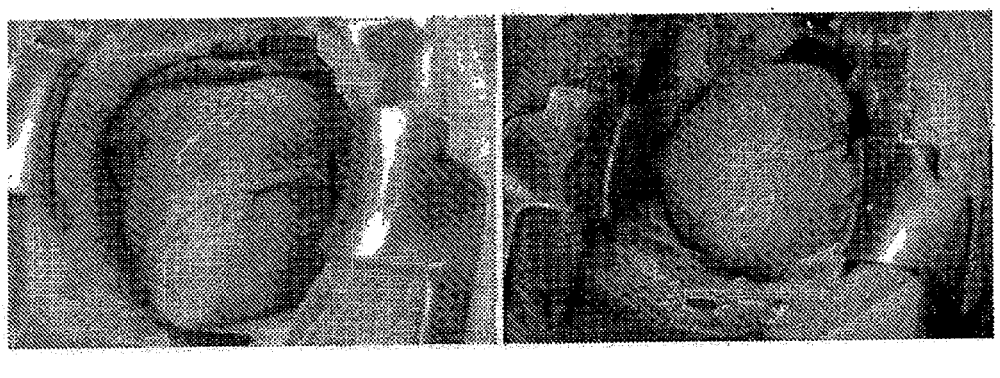
FIG. 4 is a photograph showing the heart after thoracotomy. The white portion shows a site of cell dysfunction.

A photograph of the heart after thoracotomy is shown in FIG. 4. In the photograph, the white portion indicates a cell dysfunction site. In the control group, a white cell dysfunction site was recognized throughout the ischemic region, while in the MK administration group, normal cardiac muscle was remained as a frosted state. This result shows that the myocardial cell dysfunction by ischemia and reperfusion was suppressed by administration of MK to the blood.

Figure 5:
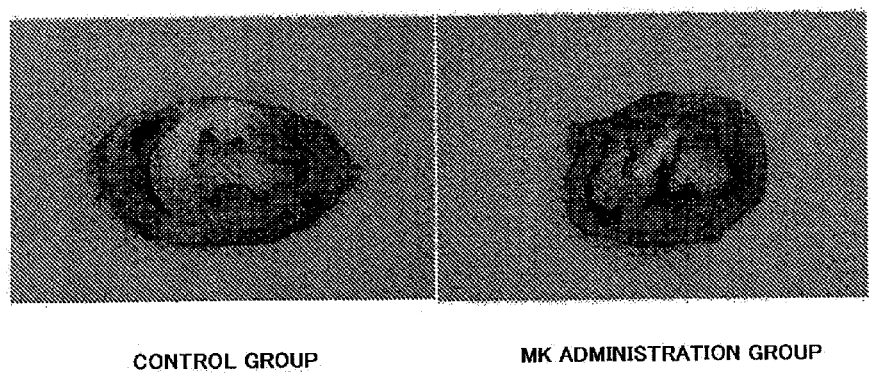
FIG. 5 shows a result of staining of a left ventricular section with Evans blue and TTC. The blue region stained with Evans blue shows a normal region, and the red region stained with TTC shows an ischemic but not infarct or necrotic region.

The result of staining the ischemic risk region of the left ventricle with Evans blue and TCC is shown in FIG. 5. In FIG. 5, the blue region stained with Evans blue indicates a normal region, and the other region indicates an ischemic risk region. In the ischemic risk region, the white region not stained red by TTC indicates an infarct region (cell dysfunction region). From FIG. 5, it was confirmed that in the control group, the white infarct region accounts for a very large region, while in the MK administration group, the white infarct region is small. The pathological sample shows that the myocardial injury area was significantly reduced in the MK therapeutic group.

Figure 6:
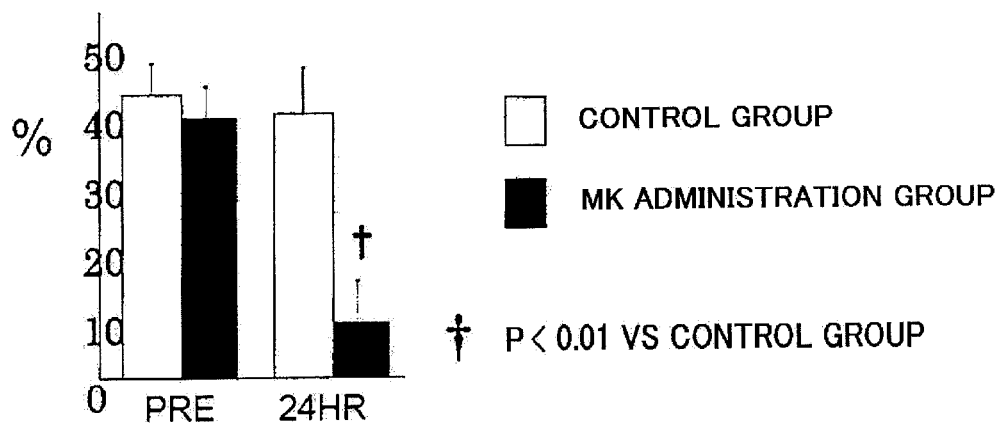
FIG. 6 shows a graph showing the ratio of infarct region/ischemic risk region (IS/AAR). In the graph, the vertical axis shows the infarct region/ischemic risk region. On the horizontal axis, PRE means before occlusion, and 24 HR means 24 hours after relief of occlusion.

The ratio of the infarct region (infarct size)/ischemic risk region (area at risk) (IS/AAR) is shown in FIG. 6. As shown in FIG. 6, the IS/AAR in the MK administration group was significantly improved as compared with that in the control group about 24 hours after relief of coronary occlusion. From this result, it was revealed that the cell dysfunction due to ischemia is significantly suppressed by administration of MK to the blood.

Figure 7:
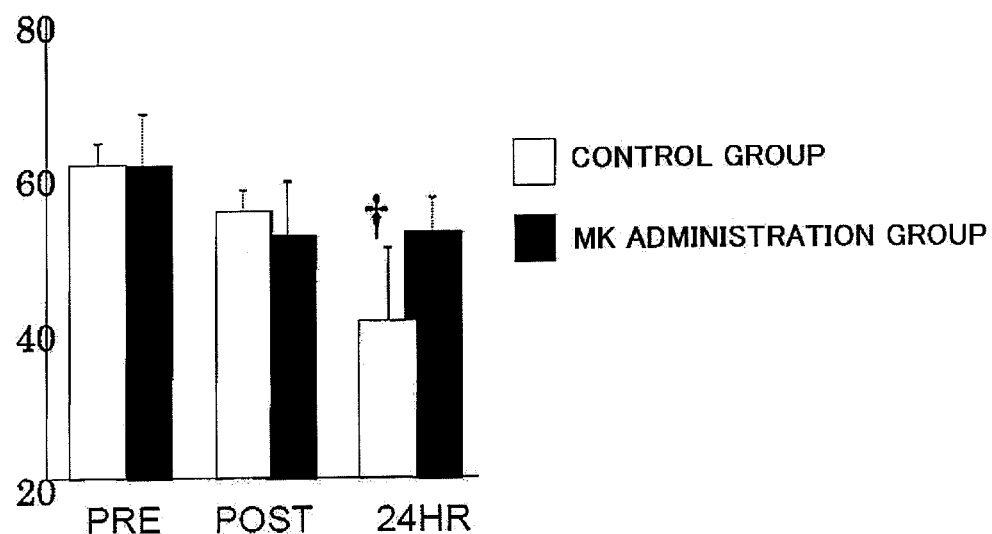
FIG. 7 is a graph showing the left ventricular ejection fraction (LVG EF). In the graph, the vertical axis shows the left ventricular ejection fraction. On the horizontal axis, PRE means before occlusion, POST means just after occlusion, and 24 HR means 24 hours after relief of occlusion.
Figure 8:
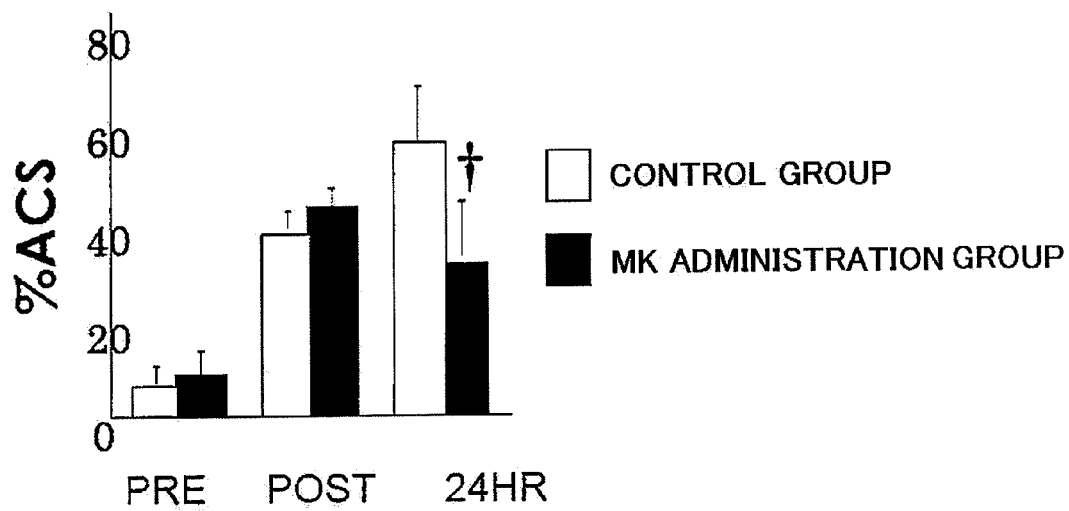
FIG. 8 shows a graph showing the percentage of abnormally contracting segment (% ACS). In the graph, the vertical axis shows the percentage of abnormally contracting segment. On the horizontal axis, PRE means before occlusion, POST means just after occlusion, and 24 HR means 24 hours after relief of occlusion.

Left ventricular ejection fraction (LVEF) (stroke volume/end-diastolic volume) and percentage of abnormally contracting segment (% ACS), calculated from the results of left ventriculography and stroke volume (SV) are shown in FIGS. 7 and 8, respectively. As shown in these graphs, the LVEF and % ACS in the MK administration group were significantly improved about 24 hours after relief of coronary occlusion as compared with the control group.

Figure 9:
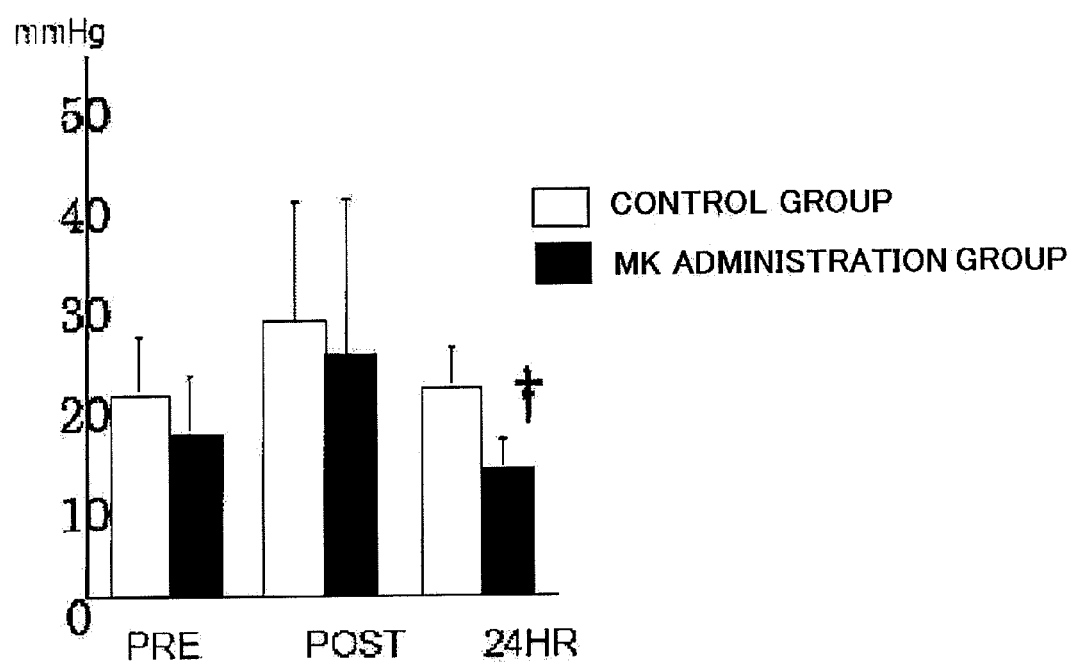
FIG. 9 shows a graph showing the left ventricular end diastolic pressure (LVEDp). In the graph, the vertical axis shows the left ventricular end diastolic pressure. On the horizontal axis, PRE means before occlusion, POST means just after occlusion, and 24 HR means 24 hours after relief of occlusion.

The result of measurement of the left ventricular end diastolic pressure (LVEDp) with the pig tail catheter is shown in FIG. 9. As shown in FIG. 9, the MK administration group showed a significant decrease in left ventricular end diastolic pressure as compared with the control group.

Figure 10:
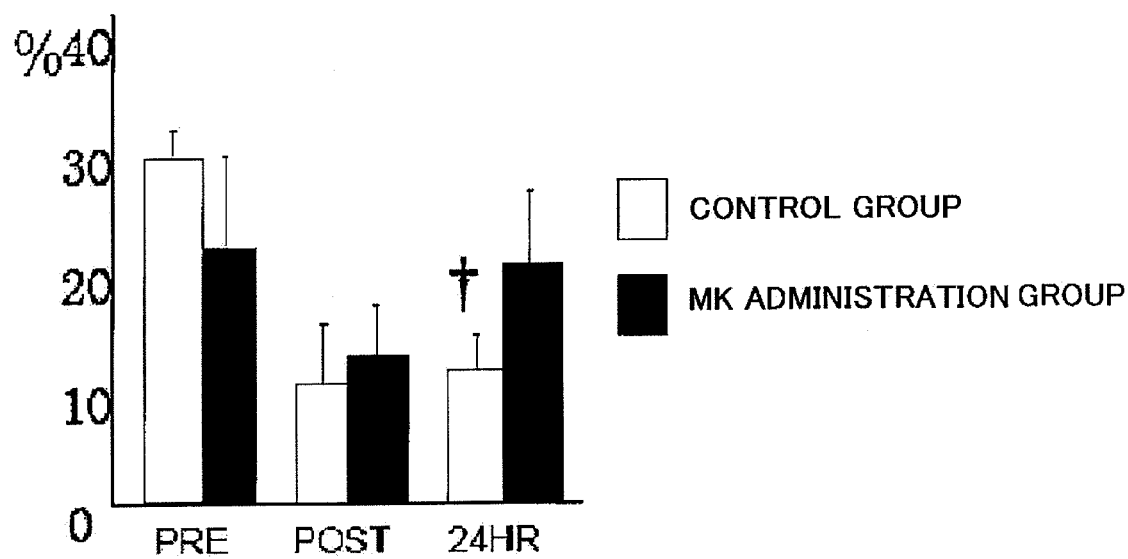
FIG. 10 shows a graph showing the percentage of interventricular septum thickening (% IVST). In the graph, the vertical axis shows the percentage of interventricular septum thickening. On the horizontal axis, PRE means before occlusion, POST means just after occlusion, and 24 HR means 24 hours after relief of occlusion.

The result of measurement of the percentage of interventricular septum thickening (% IVST) by ultrasonography is shown in FIG. 10. As shown in FIG. 10, the MK administration group showed significant recovery in percentage of interventricular septum thickening as compared with the control group.

Figure 11:
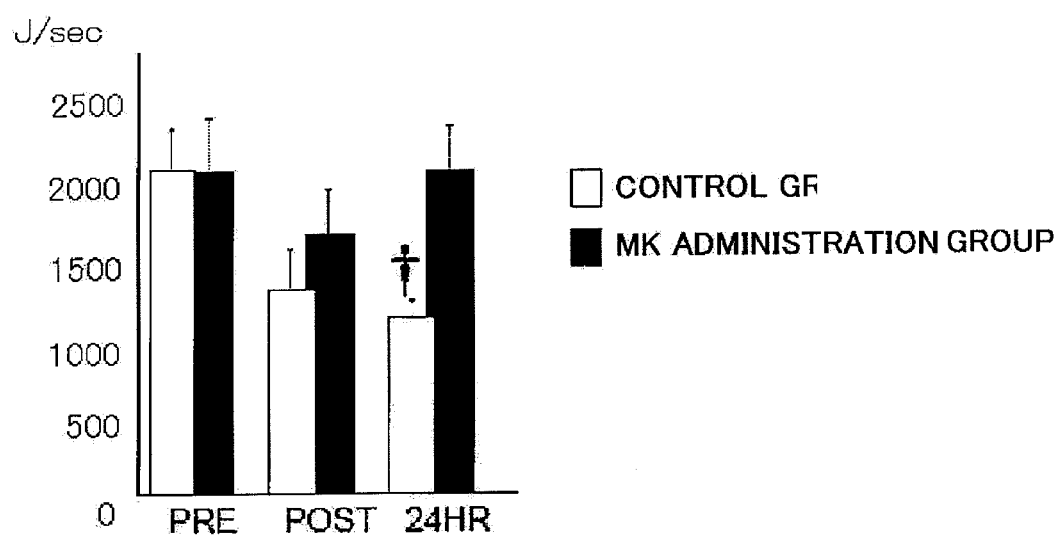
FIG. 11 shows a graph showing the maximum value of pressure derivative (dP/dTmax or peak dP/dT). In the graph, the vertical axis shows the maximum value of pressure derivative. On the horizontal axis, PRE means before occlusion, POST means just after occlusion, and 24 HR means 24 hours after relief of occlusion.

The calculated maximum value of pressure derivative (dP/dTmax or peak dP/dT) indicating the left ventricular systolic rate is shown in FIG. 11. As shown in FIG. 11, the MK administration group showed significant suppression in loss of dP/dT as compared with the control group.

Figure 12:
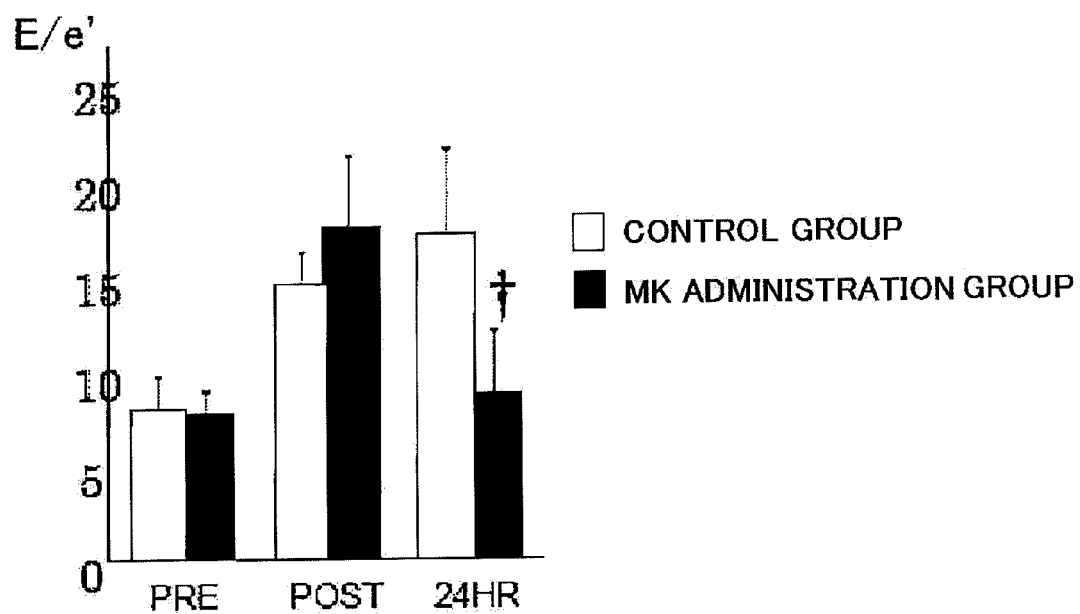
FIG. 12 shows a graph showing E/e' values calculated from a result of ultrasonography. In the graph, the vertical axis shows the calculated E/e' values. On the horizontal axis, PRE means before occlusion, POST means just after occlusion, and 24 HR means 24 hours after relief of occlusion.

To evaluate the diastolic ability of the left ventricle, the moving speed of mitral annulus was measured by tissue Doppler method in cardiac ultrasonography, and the E/e' value was calculated from the crest values of measured E wave and e' wave. The result is shown in FIG. 12. The E wave of the transmitral flow pattern was increased with the progress of heart failure. An increase in E/e' can be diagnosed as heart failure having an increased left ventricular end-diastolic pressure. As shown in FIG. 11, the MK administration group showed significant suppression in increase of left ventricular end-diastolic pressure as compared with the control group.

Figure 13:
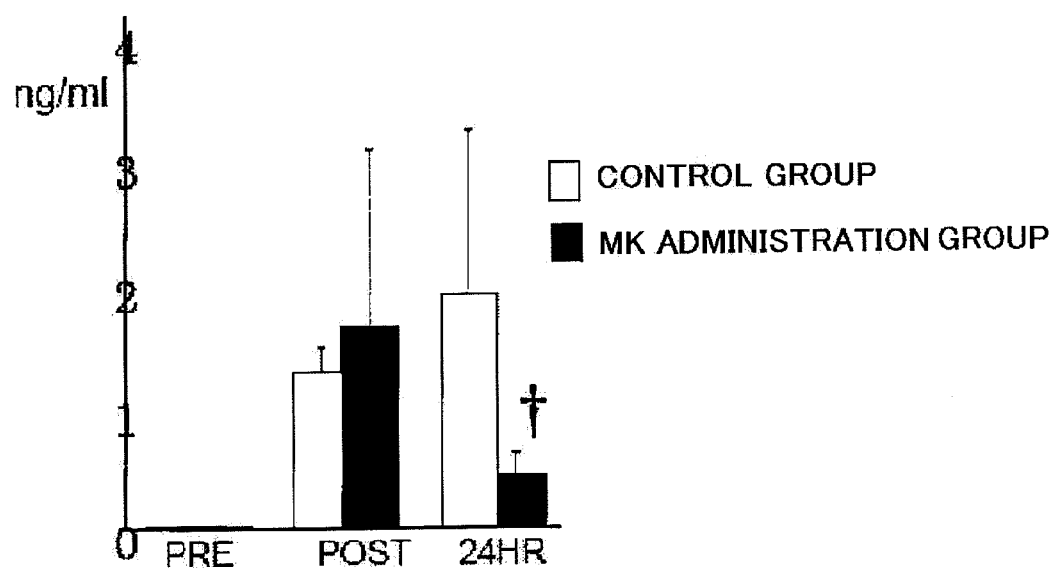
FIG. 13 shows a graph showing the concentration of troponin T in blood. In the graph, the vertical axis shows the concentration of troponin T in blood. On the horizontal axis, PRE means before occlusion, POST means just after occlusion, and 24 HR means 24 hours after relief of occlusion.

The concentration of troponin T measured in blood test is shown in FIG. 13. Troponin T is one of contraction-regulating proteins contained in cardiac muscle, and when cardiac muscle is damaged, troponin T is released from cytoplasm to blood and detected in a blood test. As a result of this experiment, the troponin T value in the MK treatment group showed a significantly low value 24 hours after constriction, as shown in FIG. 13.

The survival rate of pigs during the experiment was 55.6% (4 of 9 pigs were dead) in the control group, and was 85.7% (1 of 7 pigs was dead) in the MK administration group indicating that the MK administration group was superior to the control group in survival rate as well.

Example 2

Therapeutic Effect of Intracoronary Administration of MK on Myocardial Cell Dysfunction After Ischemia-Reperfusion (Administration After Occlusion)

(1) Preparation of MK, Creation of an Ischemic Model Animal, and Administration of MK Human MK was prepared in the same manner as described in Example 1. The same experiment as described in Example 1 was carried out except that a model animal was administered continuously with 5 μg/kg MK or physiological saline 5 to 10 minutes after cancellation of occlusion.

(2) Results

It was revealed that no significant difference was recognized in the cases where administration was initiated during occlusion and in the cases where administration was initiated after relief of occlusion from both of the results of the MK administration group and the physiological saline administration group. This result indicated that administration after relief of occlusion also achieves the therapeutic effect of MK on cell dysfunction (not shown).

Example 3

Detection of an Accumulated Site of MK by Intracoronary Administration (1) Preparation and Administration of Fluorescence-Labeled MK Human MK was prepared in the same manner as described in Example 1. A fluorescent dye rhodamine was bound to the prepared MK to give fluorescence-labeled MK. The florescence-labeled MK was administered to a pork pig (male, about 40 kg) in the same manner as described in Example 1. 24 hours after administration, the heart was removed and myocardial tissue was observed under a fluorescence microscope to detect accumulation of the fluorescence-labeled MK.

(2) Results

Figure 14:
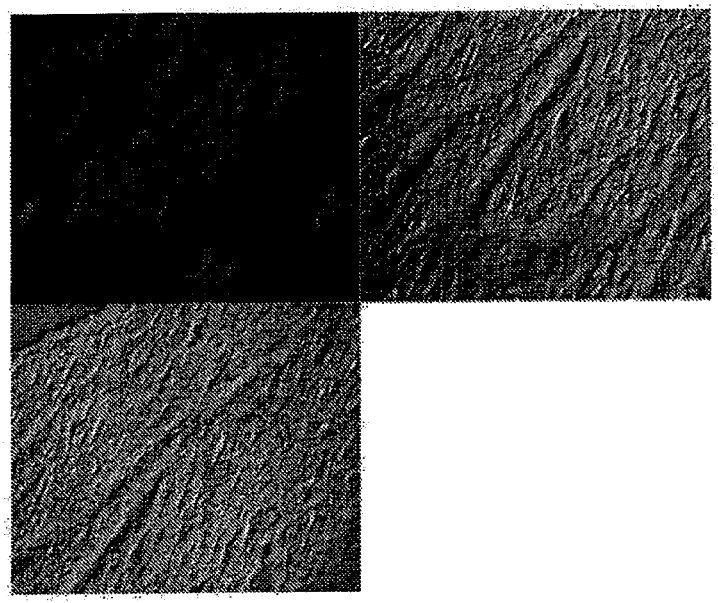
FIG. 14 is a photograph of a section of an ischemic region of a porcine heart 24 hours after relief of occlusion. Coloration (red) of fluorescence-labeled MK is shown at the upper left, and the myocardial tissue in the same visual field is shown at the upper right. A superimposed image of the two is shown at the lower left. Strong coloration of fluorescence-labeled MK injected via coronary artery is recognized in the ischemic region of cardiac muscle.
Figure 15:
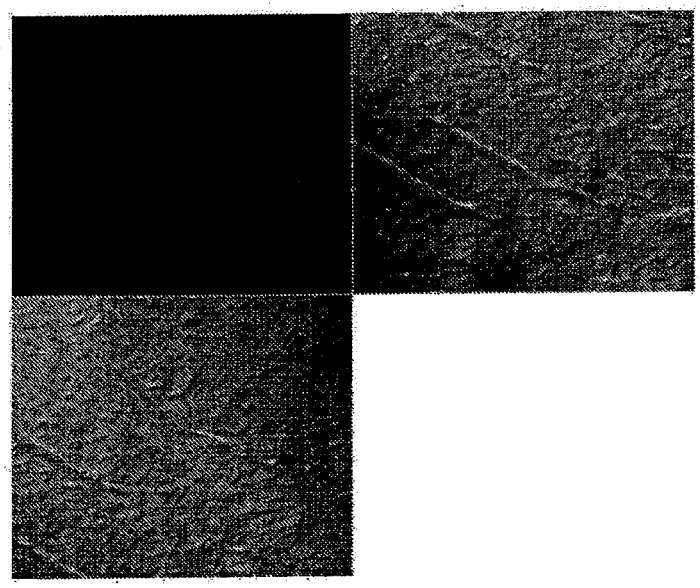
FIG. 15 is a photograph of a section of a non-ischemic region of the same porcine heart. Coloration of fluorescence-labeled MK is shown at the upper left, and the myocardial tissue in the same visual field is shown at the upper right. A superimposed image of the two is shown at the lower left. Coloration of fluorescence-labeled MK is hardly recognized in the non-ischemic region.

The results are shown in FIGS. 14 and 15. As shown in FIG. 14, the fluorescence-labeled MK was accumulated in the damaged myocardial site of the porcine heart, while as shown in FIG. 15, the fluorescence-labeled MK was not accumulated in a normal site of the porcine heart. From this result, it was revealed that MK administered via an coronary artery at the time of heart damage was accumulated specifically in the damaged portion of the cardiac muscle.

Example 4

Detection of an Accumulated Site of MK by Intravenous Administration (1) Preparation and Administration of Fluorescence-Labeled MK Human MK was prepared in the same manner as described in Example 1. A fluorescent dye rhodamine was bound to the prepared MK to give fluorescence-labeled MK. A mouse with the genetic background of C57BL/6 was anesthetized by intraperitoneal administration of pentobarbital (100 mg/kg) and maintained with a respirator (model SN-480-7). After thoracotomy, the left anterior descending coronary artery (LAD) was ligated by PE-10 tube. One hour after ligation, the ligated portion was removed to restore blood flow, and the mouse was used as a model animal. Just after blood flow was restored, the fluorescence-labeled MK was administered intravenously, and 24 hours after administration, organs were removed, and the accumulation of the fluorescence-labeled MK in each tissue was detected under a fluorescence microscope.

(2) Results

Figure 16:
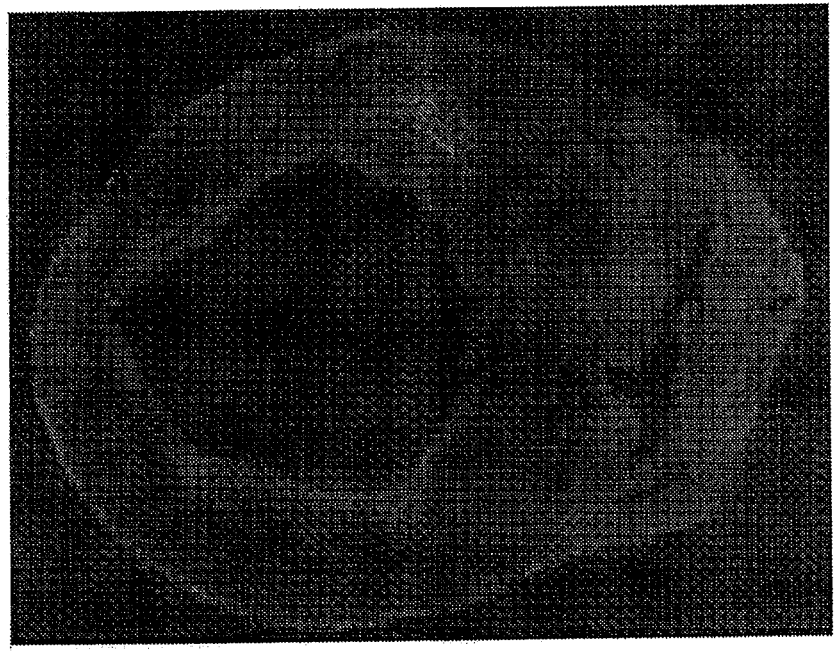
FIG. 16 is a photograph showing the fluorescence-labeled MK in a mouse heart section 24 hours after relief of occlusion.
Figure 17:
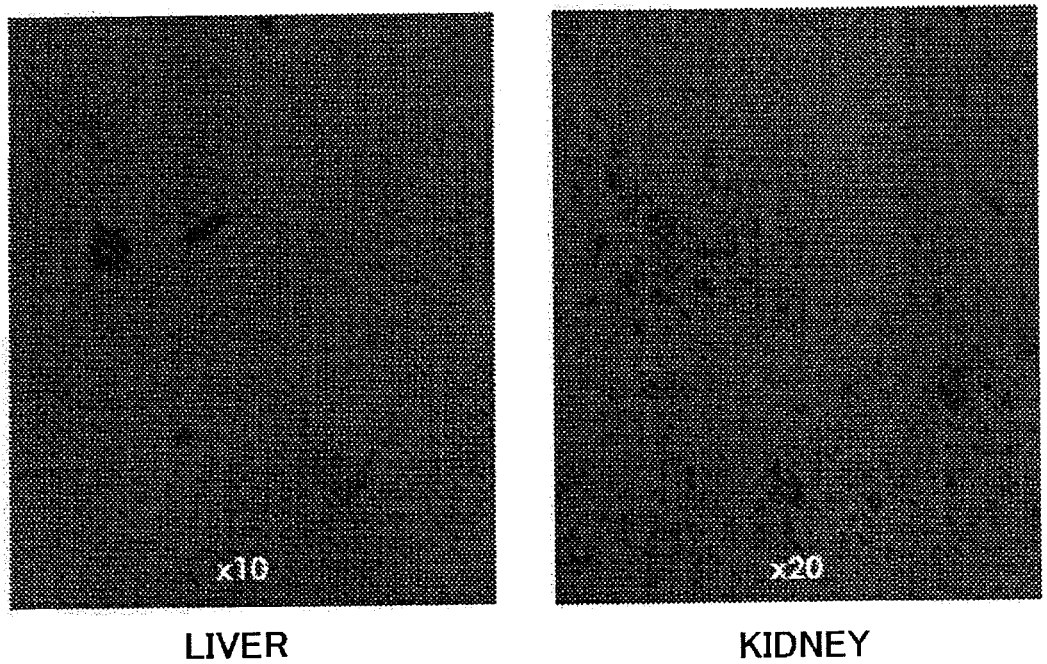
FIG. 17 is a photograph showing the fluorescence-labeled MK in mouse liver (left) and kidney (right) sections 24 hours after relief of occlusion.

The results are shown in FIGS. 16 and 17. As shown in FIG. 16, the fluorescence-labeled MK was accumulated in the damaged myocardial site of the heart, while the fluorescence-labeled MK was not accumulated in a normal site of the heart. As shown in FIG. 17, the fluorescence-labeled MK was not accumulated in non-heart organs such as liver and kidney. From this result, it was revealed that even when MK was intravenously administered, MK accumulated specifically in the damaged myocardial site of the heart, and thus the myocardial cell dysfunction can be prevented or treated even by intravenous administration.

Example 5

Measurement of the Ability of MK to Activate eNOS in a Hypoxic/Reoxygenated Model of Human Umbilical Vein Endothelial Cells (HUVEC)

(1) Hypoxic/Reoxygenated HUVEC and Administration of MK

HUVECs (HUVEC Pooled Cambrex CCS 2519) obtained from TAKARA BIO INC. were seeded at $6.0 \times 10^5$ cells/well on a 35×10 mm dish (BD Falcon 351008). 2.5 mL of a complete medium of EBM-2 (Cambrex corporation) was added to each well and the cells were cultured for 4 hours under the conditions of 20% $O_2$, 5% $CO_2$ and 37° C. Thereafter, the EBM-2 medium was exchanged with a growth factor-free medium and the cells were cultured for 9 hours under the conditions of 20% $O_2$, 5% $CO_2$ and 37° C. and then for 3 hours under hypoxic conditions of 95% $N_2$, 5% $CO_2$ and 37° C. Then, MK prepared in the same manner as described in Example 1 was diluted to a concentration of 100 ng/mL with EBM-2 medium and then added at 2.5 mL/well to the MK administration group, while a control substance was added at 2.5 mL/well to the control group, and then the cells were cultured again for 3 hours under the conditions of 20% $O_2$, 5% $CO_2$ and 37° C. After culture was finished, the cells were recovered, homogenized and subjected to immunoblotting to examine bands of intracellular eNOS and intracellular phosphorylated eNOS (phosphorylation of serine at position 1177).

(2) Results

Figure 18:
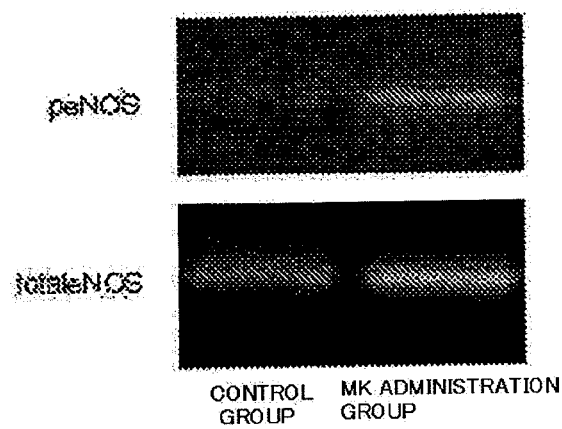
FIG. 18 is the result of western blotting analysis of hypoxic/reoxygenated HUVEC showing bands of eNOS and phosphorylated eNOS (peNOS).
Figure 19:
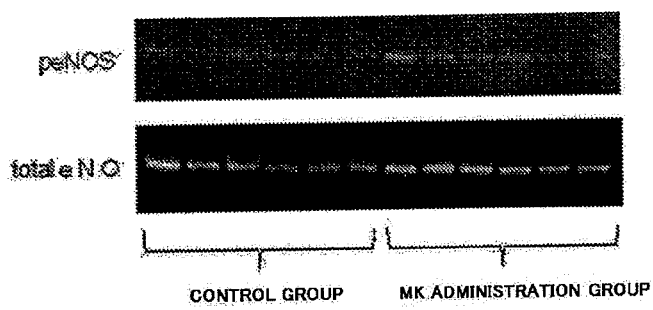
FIG. 19 is the result of western blotting analysis of hypoxic/reoxygenated HUVEC showing bands of eNOS and phosphorylated eNOS (peNOS).

The results are shown in FIGS. 18 and 19. As shown in these figures, significant phosphorylation of eNOS was observed in the MK administration group as compared with the control group in this experiment. Because the hypoxic conditions used in this experiment are an experimental model of ischemic conditions, it was revealed from the results of this experiment that under the ischemic conditions, MK causes phosphorylation of eNOS. Because phosphorylation of eNOS is also known to cause vasodilation, MK is considered to exhibit a cellular protection action, via phosphorylation of eNOS, against ischemic disorder.

Example 6

Porcine Arterial Dilation Test (1) Measurement of Porcine Coronary Artery

After porcine coronary angiography, MK (5 μg/kg) was administered continuously for 10 minutes via the lumen of a PTCA wire into the coronary artery in the same manner as described in Example 1. After administration, coronary angiography was conducted again, and the state of the porcine coronary artery was compared before and after administration of MK.

(2) Results

Figure 20:
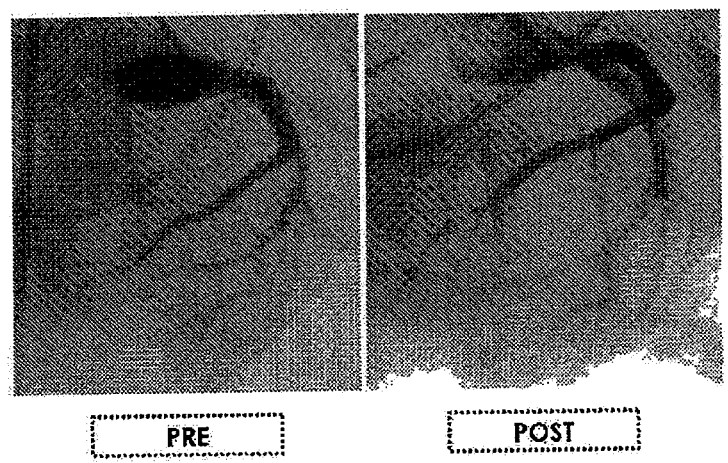
FIG. 20 shows photographs of porcine coronary angiography before and after administration of MK. Under the photograph, PRE means before administration of MK, and POST means after administration of MK.

The result is shown in FIG. 20. PRE shows coronary angiography before intracoronary injection of MK, and POST shows coronary angiography after intracoronary injection of MK. From these results of coronary angiography, clear dilation of the coronary arteries and capillary vessels was visually recognized angiographically after administration of MK.

Example 7

Rat Blood Pressure Test (1) Administration of MK and a Method of Measuring Blood Pressure The thorax of a rat (Wister, SLC Ltd.) after endotracheal intubation was opened under controlled artificial respiration. After the heart was exposed, an intracardiac pressure measuring catheter (Millar Ltd.) was inserted through the cardiac apex. After a route of drip infusion was secured in a postcaval vein, MK (5 μg/kg, 50 μg/kg, 500 μg/kg) was continuously injected, and a real time fluctuation of blood pressure was measured with the Millar catheter.

(2) Results

Figure 21:
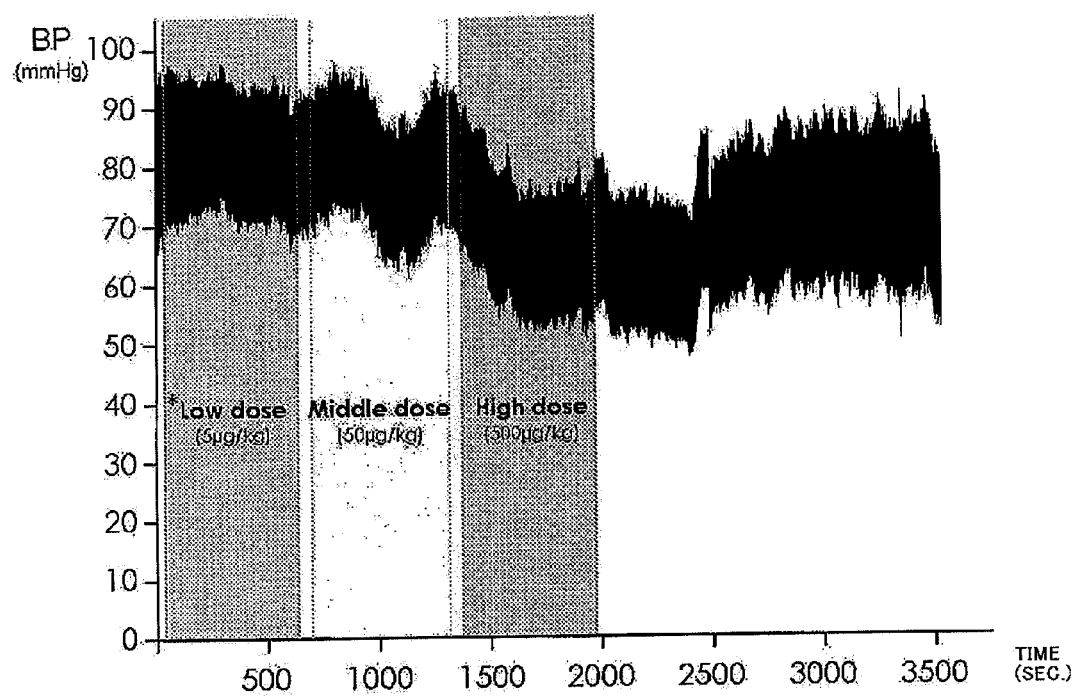
FIG. 21 is a graph of blood-pressure change by MK administration. The vertical axis shows blood pressure and the horizontal axis shows time. Low dose shows a period of administration of midkine at a dose of 5 µg/kg, Middle dose shows a period of administration of midkine at a dose of 50 µg/kg, and High dose shows 500 µg/kg.

The results are shown in FIG. 21. In this experiment, it was confirmed that the blood pressure was reduced by administering 500 μg/kg MK intravenously to the rat.

Industrial Applicability

The therapeutic or prophylactic agent of the present invention is useful as a drug for preventing or treating ischemic disorder or myocardial cell dysfunction after ischemia-reperfusion.

The invention claimed is:

1. A method to activate nitric oxide synthase (eNOS) which method comprises contacting a vascular endothelial cell expressing said eNOS with a composition comprising a human midkine protein as an active ingredient.

2. The method of claim 1 wherein said eNOS is contained in a subject in need of activation of said eNOS and said contacting comprises administering said composition to the subject.

3. A method to stimulate vasodilation in a subject in need of said stimulation of vasodilation which method comprises administering to the coronary artery of a subject in need of such stimulated vasodilation a composition comprising a human midkine protein as an active ingredient.

4. The method of claim 3 wherein said subject has an ischemia disorder or muscle cell dysfunction after ischemia perfusion.

5. The method of claim 3 wherein said administering is to the coronary artery of the subject comprises delivery of the human midkine protein via the lumen of a percutaneous transluminal coronary angioplasty (PTCA) device into a coronary artery of the subject.

6. The method of claim 2 wherein said composition is administered in an amount of 50 ng/kg to 100 μg/kg.

7. The method of claim 3 wherein said composition is administered in an amount of 50 ng/kg to 100 μg/kg.

* * * * *

UNITED STATES PATENT AND TRADEMARK OFFICE
CERTIFICATE OF CORRECTION

PATENT NO. : 8,288,343 B2
APPLICATION NO. : 12/593277
DATED : October 16, 2012
INVENTOR(S) : Mitsuru Horiba et al.

It is certified that error appears in the above-identified patent and that said Letters Patent is hereby corrected as shown below:

In the Specification:

At column 5, line number 37, please change "100 pg/kg" to --100 µg/kg--

In the Claims:

At column 16, claim number 1, line number 35, please change "nitric oxide synthase" to --endothelial nitric oxide synthase--

Signed and Sealed this
Twenty-ninth Day of September, 2015

Michelle K. Lee
*Director of the United States Patent and Trademark Office*